United States Patent [19]

Sugiura et al.

[11] Patent Number: 4,842,860

[45] Date of Patent: Jun. 27, 1989

[54] PROCESS FOR PRODUCING CONTROLLED RELEASE PREPARATION

[75] Inventors: Hisao Sugiura; Masanori Watanabe, both of Ube, Japan

[73] Assignee: Ube Industries, Ltd., Ube, Japan

[21] Appl. No.: 65,770

[22] Filed: Jun. 23, 1987

[30] Foreign Application Priority Data

Jul. 1, 1986 [JP] Japan .................. 61-152625

[51] Int. Cl.$^4$ ............................. A01N 25/34
[52] U.S. Cl. .................. 424/403; 424/84; 424/76.1; 424/76.8
[58] Field of Search ............ 424/408, 471–473, 424/76.1, 76.8, 84

[56] References Cited

U.S. PATENT DOCUMENTS

| | | | |
|---|---|---|---|
| 4,017,030 | 4/1977 | Coplan et al. | 239/44 |
| 4,369,172 | 1/1983 | Schor et al. | 424/480 X |
| 4,698,264 | 10/1987 | Steinke | 424/408 X |

FOREIGN PATENT DOCUMENTS

| | | |
|---|---|---|
| 56-95101 | 8/1981 | Japan . |
| 56-142202 | 11/1981 | Japan . |
| 57-009705 | 1/1982 | Japan . |
| 57-045101 | 3/1982 | Japan . |
| 58-113102 | 7/1983 | Japan . |

OTHER PUBLICATIONS

American Chem. Society, 33 (1976) p. 283, Controlled Release of Pheromones Through Multi-Layered Polymeric Dispensers–Merton Beroza.

*Primary Examiner*—Michael Lusignan
*Attorney, Agent, or Firm*—Frishauf, Holtz, Goodman & Woodward

[57] ABSTRACT

Disclosed is a process for producing a controlled release preparation, which comprises:
  mixing a resin with a carrier;
  impregnating the resulting mixture with a drug; and
  applying pressure to the mixture to form a solid.

The controlled release preparation according to this invention can securely and stably release a drug for a desired period of time.

9 Claims, No Drawings

PROCESS FOR PRODUCING CONTROLLED RELEASE PREPARATION

BACKGROUND OF THE INVENTION

This invention relates to a process for producing a controlled release preparation, more particularly to a process for producing a controlled release preparation which volatilizes drugs or active agent such as an insecticide, an attractant, a repellent, a pheromone, an insect controlling agent, a bactericide, flavor and a deodorizer, little by little over a prolonged period of time, which are widely employed in the agricultural, domestic and business fields.

Various methods have been proposed to control the effect of an active agent or of a drug over a prolonged period of time even when it is administered in small amounts (release controlling method). Namely, there have been known methods to use a hollow tube (U.S. Pat. No. 4,017,030, Japanese Provisional Patent Publication Nos. 142202/1981, 9705/1982, 45101/1982, etc.); to employ a microcapsule (U.S. Pat. Nos. 2,800,457, 2,800,458, 3,577,515, etc.); and to employ a laminated film (*American Chemical Society*; 33 (1976) pp 283), etc.

However, in all of the above methods, preparation processes are so complicated and costly that they suffer significant disadvantage in providing controlled release drugs for uses particularly in the agricultural and domestic field. Namely, in the above method employing a hollow tube, filling and packing processes are complicated and costly, and also in the above method employing a microcapsule or a laminated film, the manufacturing process is complicated and costly. Also, there may be mentioned a method to use a solid composition (Japanese Provisional Patent Publication Nos. 95101/1981 and 113102/1983), wherein release controlling effect is achieved by use of a film formed by heating a solid and a resin. However, any of methods described above includes a complicated manufacturing processes, and thus is liable to be costly.

Thus, the present inventors have made extensive studies in an attempt to provide a controlled release preparation at low costs, and as a result accomplished this invention.

SUMMARY OF THE INVENTION

This invention relates to a process for producing a controlled release preparation, which comprises mixing a resin with a carrier; impregnating the resulting mixture with a drug or active agent; and then compressing the mixture to form a solid.

DETAILED DESCRIPTION OF THE PREFERRED EMBODIMENTS

The resin to be used in this invention may be provided bin any form, so long as it can be impregnated with a drug, and usually it is used in the form of powder or granule. Said resin, which may be used, includes homopolymers of polyethylene, polypropylene, nylon, polyvinyl chloride, polyvinyl acetate or cellulose derivatives, or copolymers of such homopolymers with other monomers or oligomers.

The drug or active agent to be used in this invention includes insecticides, attractants, repellents, pheromones, insect controlling agents, bactericides, flavors, deodorizers, etc. They may also be used as a mixture of two or more kinds.

The carrier to be used in this invention is not particularly limited so long as a mixture of the carrier, the drug or active agent and the resin can be solidified into a shape by application of pressure and its shape can be retained, and is exemplified by cellulose, silicic acid, kaolin, diatomaceous earth, starch, rice polishings, fish meal, wood flour, chitin, chitosan, cyclodextrin, activated carbon, etc. Such carriers may be used singly or as a mixture of two or more kinds.

In this invention, the mixing ratio of the resin to the carrier may be in the range of 2:1 to 1:100 (resin : carrier), preferably 1:1 to 1:20 in terms of weight ratio.

If the ratio of the resin to the carrier is too large, the solid obtained by compression and solidification is liable to crack upon exposure to physical and external pressure. Also, the resin to be employed in this invention has a function as a release controlling body which absorbs a drug or active agent once and then releases it gradually in atmosphere. Accordingly, if the ratio of the resin to the carrier is too large, the release controlling period of said drug or active agent may be too long, thereby the amount of the drug or active agent to be released per unit period may be too small. Alternatively, if the ratio of the rein to the carrier is too small, the release controlling period of said drug or active agent may be too short, thereby the amount of the drug or active agent to be released per unit period may be too large, exhibiting no sufficient release controlling effect.

The controlled release preparation may be provided in any form, so long as it can exhibit sufficient release controlling effect, preferably in the form of tablet or pill, more preferably in the form of tablet.

The process for impregnating the resin and the carrier with a drug in this invention is not particularly limited. One of the resin and the carrier may be impregnated with the drug first and then the other may be added thereto; alternatively, a mixture of the resin and the carrier may be impregnated with the drug. While the drug may be employed as such for the impregnation, it may also be dissolved in a suitable solvent prior to the impregnation. The ratio of said drug to the resin and carrier is not particularly limited and depends on the nature of the drug and the purpose for which it is used.

The shape and size of the solid obtained by application of pressure and solidification may be varied depending on the occasion of application and purposes. The pressure to be applied in solidification of the mixture may not be particularly limited and can suitably be selected depending on the kind of the drug, usage, the kinds of the carrier and the resin and the mixing ratio thereof, shape of the solid, etc.

In this invention, if necessary, suitable amounts of an antioxidant, an ultraviolet screening (absorbing) agent, a colorant or a lubricant may be added to said mixture in addition to the drug, resin and carrier.

When a solid is produced on an industrial scale according to this invention, it may be produced easily by means of a commonly available tablet machine and the like. Also, hermetical packing of the thus obtained solid may be achieved by use of a very commonly available packing equipment to obtain it as a separately packed preparation. Accordingly, this invention can provide an inexpensive drug or active agent having a release controlling property.

The controlled release preparation to be obtained according to the process of this invention can securely and stably release the drug or active agent for a desired period of time.

EXAMPLE

This invention will be illustrated in more detail by referring to Examples and Comparative Example, but they are not construed to limit the scope of this invention.

Example 1

1.0 kg of ethylene-vinyl acetate copolymer powder (UM-8430, trade name, produced by Ube Industries, Ltd.) was mixed with 4.0 kg of cellulose powder, and 5 mg of periplanone B which is a sex pheromone of Periplaneta (as a solution in 300 ml of hexane) was added thereto, and the resulting mixture was mixed using a mixer. The resulting mixture was made into tablets using a rotary tablet machine to obtain 10,000 pieces of solids each weighing 0.5 g. One of the thus obtained solids was used as a sample to carry out bioassay and its controlled release property was examined.

The bioassay was conducted using 50 imagoes of male Periplaneta in a plastic box with a size of $50 \times 40 \times 30$ cm (height). A shelter was provided in the corner of the box, and it was confirmed that the Periplanetas usually stay in the shelter. Imagoes of male Periplaneta are known to be attracted by periplanone B which is a sex pheromone and take a specific posture with their alae open. In the bioassay on effects of pheromone, a method of counting the number of Periplanetas attracted thereby is generally used, and in this Example also the same method was employed. Namely, the above sample was placed in the plastic box mentioned above, and the number of Periplanetas attracted thereby was counted. It should be noted that the samples were left to stand in a thermostatic chamber set at 40° C. except when bioassay was conducted. Bioassay was conducted every two days, and the days over which attracting effect lasted was defined as controlled release lasting days. As a result, lasting days of release controlling was found to be 36 days.

As a control, 0.5 $\mu$g of periplanone B (as a hexane solution) as such was allowed to stand in a thermostatic chamber set at 40° C. As a result of the bioassay, it was found that attracting effect was lost in one day.

Example 2

The same procedure was carried out as in Example 1, except that the mixing ratio of the powder of ethylenevinyl acetate copolymer to the cellulose powder was 1:19. Lasting days of release controlling was found to be 26 days.

Example 3

The same procedure was carried out as in Example 1, except that one of the solids as obtained in Example 1 was hermetically sealed with a packing paper and left to stand in a thermostatic chamber of 50° C. for 42 days and then unpacked for bioassay. Lasting days of release controlling was found to be 34 days.

Example 4

The same procedure was carried out as in Example 1, except that a mixture of cellulose and starch at a ratio of 2:1 was used as a carrier. Lasting days of release controlling was found to be 28 days.

Example 5

The same procedure was carried out as in Example 1, except that a mixture of cellulose and parched rice polishings at a ratio of 2:1 was used as a carrier. Lasting days of release controlling was found to be 32 days.

Comparative Example 1

The same procedure was carried out as in Example 1, except that periplanone B was added to a cellulose powder alone without addition of a resin. Lasting days of release controlling was found to be 6 days.

According to this invention, an inexpensive controlled release preparation may be provided using a simple means.

We claim:

1. A process for producing a controlled release preparation, which comprises:
    mixing a resin selected from the group consisting of polyethylene, polypropylene, nylon, polyvinyl chloride, and polyvinyl acetate, with a carrier in a ratio of resin to carrier of 2:1 to 1:100 by weight;
    impregnating the resulting mixture with an effective amount of an active agent; and
    applying pressure to the mixture to form a solid; and wherein said resin, said carrier and said active agent are mutually exclusive substances.

2. The process according to claim 1, wherein said solid is in the form of a tablet.

3. The process according to claim 1, wherein said resin is in the form of powder or granule.

4. The process of claim 1 wherein said carrier is cellulose, silicic acid, kaolin, diatomaceous earth, starch, rice polishings, fish meal, wood flour, chitin, chitosan, cyclodextrin, or activated charcoal.

5. The process according to claim 1, wherein the mixing ratio of the resin to the carrier is 1:1 to 1:20.

6. The process according to claim 1, wherein said active agent is selected from the group consisting of an insecticide, an attractant, a repellent, a pheromone, an insect controlling agent, a bactericide, a flavor, a deodorizer and a mixture of two or more kinds thereof.

7. The process according to claim 6 wherein said carrier is cellulose, silicic acid, kaolin, diatomaceous earth, starch, rice polishings, fish meal, wood flour, chitin, chitosan, cyclodextrin, or activated charcoal.

8. The process of claim 7 wherein the mixing ratio of the resin to the carrier is 1:1 to 1:20.

9. The process according to claim 4 wherein the mixing ratio of the resin to the carrier is 1:1 to 1:20.

* * * * *